United States Patent
Wu et al.

(10) Patent No.: US 7,494,986 B2
(45) Date of Patent: Feb. 24, 2009

(54) CYCLOALKYLAMINE DERIVATIVES AS NK-1/SSRI ANTAGONISTS

(75) Inventors: Yong-Jin Wu, Madison, CT (US); Huan He, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 319 days.

(21) Appl. No.: 11/183,699

(22) Filed: Jul. 18, 2005

(65) Prior Publication Data
US 2006/0019992 A1 Jan. 26, 2006

Related U.S. Application Data

(60) Provisional application No. 60/589,730, filed on Jul. 20, 2004.

(51) Int. Cl.
*A01N 43/00* (2006.01)
*A61K 31/33* (2006.01)
*C07D 225/00* (2006.01)
*C07D 295/00* (2006.01)

(52) U.S. Cl. ........................... 514/183; 540/450
(58) Field of Classification Search ............... None
See application file for complete search history.

(56) References Cited

U.S. PATENT DOCUMENTS

| 6,136,824 A | 10/2000 | MacLeod et al. | |
| 7,067,507 B2 * | 6/2006 | Pulley et al. | 514/183 |

FOREIGN PATENT DOCUMENTS

| WO | WO 99/62900 | 12/1999 |
| WO | WO 2004/005255 | 1/2004 |
| WO | WO 2004/005256 | 1/2004 |
| WO | WO 2004/022539 | 3/2004 |
| WO | WO 2004/056771 | 7/2004 |

OTHER PUBLICATIONS

"Depression-signs, syptoms, help, and treatment", http://www.helpguide.org/mental/depression_signs_types_diagnosis_treatment.htm, accessed Dec. 29, 2007.*
Murthy et al. Expert Opinion on Therapeutic Patents, 1998, 8(7), 785-818.*
Dell'Osso et al. Expert Opinion on Pharmacotherapy, 2005, 6(15), 2727-40.*
Amadesi et al. American Journal of Respiratory and Critical Care Medicine, 2001, 163, 1206-11.*
Stevenson, G.I., et al., "4,4-Dissubstituted Piperidines: A New Class of $NK_1$ Antagonist", *J. Med. Chem.* 1995, 38 1264-1266.
Stevenson, G.I. et al., "4,4-Dissubstituted Piperidine High-Affinity $NK_1$ Antagonists: Structure-Activity Relationships and *in Vivo* Activity", *J. Med. Chem.* 1998, 41, 4623-4635.
Kramer, Mark S., et al., "Distinct Mechanism for Antidepressant Activity by Blockade of Central Substance P Receptors", *Science*, 281 (1998) 1640-1645.
Maubach, Karen A., et al., "Novel Strategies for Pharmacotherapy of Depression", *Current Opinion in Chemical Biology*, 3 (1999) 481-488.
Rosen, Terry J., et al., "Synthesis and Structure-Activity Relationships of CP-122,721, A Second-Generation NK-1 Receptor Antagonist", *Bioorganic & Medicinal Chemistry Letters*, 8 (1998) 281-284.
Ryckmans, Thomas, et al., "First Dual $NK_1$ Antagonists-Serotonin Reuptake Inhibitors: Synthesis and SAR of a New Class of Potential Antidepressants", *Bioorganic & Medicinal Chemistry Letters*, 12 (2002) 261-264.

* cited by examiner

*Primary Examiner*—James O Wilson
*Assistant Examiner*—Noble Jarrell
(74) *Attorney, Agent, or Firm*—James Epperson; Aldo A. Algieri

(57) ABSTRACT

The present disclosure relates to chemical compounds and their use in human therapy. A specific embodiment relates to compounds of Formula (I) or an isomer, a pharmaceutically acceptable salt or solvate thereof and pharmaceutically acceptable formulations comprising said compounds

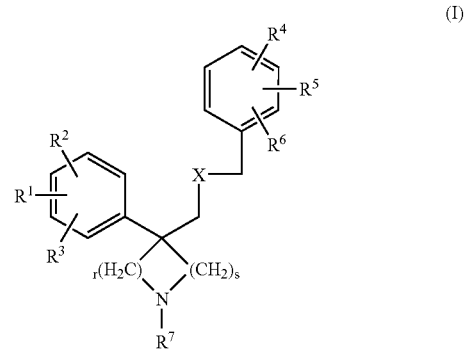

useful for the treatment or prevention of conditions mediated by tachykinins and/or selective inhibition of serotonin reuptake transporter protein. The compounds act as dual NK-1 antagonists and selective serotonin reuptake inhibitors.

7 Claims, No Drawings

CYCLOALKYLAMINE DERIVATIVES AS NK-1/SSRI ANTAGONISTS

CROSS-REFERENCE TO RELATED APPLICATIONS

This is a non-provisional application which claims the benefit of U.S. Provisional Application No. 60/589,730 filed Jul. 20, 2004.

FIELD OF THE DISCLOSURE

The present disclosure relates to novel chemical compounds and to the use of said compounds in human therapy. A particular embodiment relates to cycloalkylamine derivatives and to pharmaceutical compositions comprising said derivatives and to their medical use.

BACKGROUND OF THE DISCLOSURE

Depression is a debilitating disease causing significant mortality and affecting up to ten percent of the population. Selective serotonin reuptake inhibitors (SSRI's) have proven to be effective in treating depression, but have the disadvantages of delayed onset of antidepressant activity, limited efficacy and significant side effects. See Novel strategies for pharmacotherapy of depression, K. A. Maubach, N. M. J. Rupniak, M. S. Kramer, and R. G. Hill, *Current Opinion in Chemical Biology* 1999, 3, 491-499. Another class of clinically effective antidepressants are substance P (SP) antagonists which show high affinity and selectivity for the neurokinin 1 (NK-1) receptor. Robust antidepressant activity has been reported for two NK-1 antagonists, MK-869 (M. S. Kramer, et al., *Science* 1998, 281 1640) and CP-122,721 (T. J. Rosen, et al., *Bioorganic and Medicinal Chemistry Letters* 1998, 8, 28 and *CNS Drug News*, December, 2000, 24). NK-1 antagonists offer an alternative approach for treating depression in patients that respond poorly to the SSRI's and other available drugs.

The first dual NK-1 antagonists-serotonin reuptake inhibitors were described by Ryckmans et al. (*Bioorganic and Medicinal Chemistry Letters* 2002, 12, 261-264). Ryckmans discloses phenoxy acetamides and phenyl propionamides as NK-1 antagonists and serotonin reuptake inhibitors and the potential of a new generation of antidepressants.

U.S. Pat. No. 6,136,824 discloses piperidinyl-propane-2-derivatives which exhibit both NK-1 receptor antagonism and/or selective serotonin reuptake inhibitor (hereinafter referred to as SSRI) activity.

International Application WO2004/005256 discloses cyclic amine derivatives that exhibit both NK-1 receptor antagonism and/or SSRI activity.

International Application WO2004/005255 discloses N-benzyl-3-phenyl-3-heterocyclic-propionamide compounds as tachykinin and/or serotonin reuptake inhibitors.

The instantly recited compounds have activity as NK-1 antagonists and/or also have activity as selective serotonin reuptake inhibitors. Thus, they are of use in the treatment of conditions mediated by tachykinins and/or selective inhibition of the serotonin reuptake transporter protein. One aspect of the class of compounds of the present disclosure exhibit both NK-1 receptor antagonist and SSRI activity.

Thus, novel dual NK-1 antagonists and SSRI inhibitors effective for the treatment of numerous disorders, such as central nervous system disorders, would be advantageous.

SUMMARY

A novel class of compounds is provided that are dual NK-1 antagonists and/or serotonin reuptake inhibitors of Formula (I)

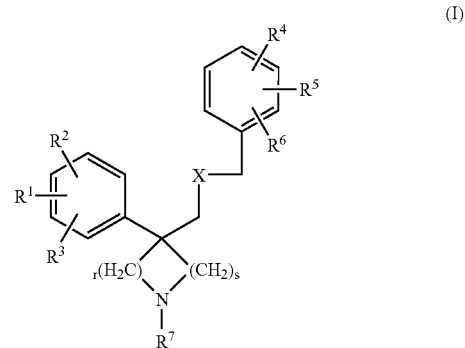

(I)

or an isomer, a pharmaceutically acceptable salt or solvate thereof wherein $R^1, R^2, R^3, R^4, R^5$ and $R^6$ independently are hydrogen, $C_{1-4}$ alkyl, $C_{1-4}$ alkoxy, fluoro$C_{1-4}$ alkyl, halogen or cyano;

X is independently selected from O, S and $NR^8$;

$R^7$ is hydrogen, $C_{1-4}$ alkyl, $C_{3-6}$ cycloalkyl, or $C_{3-6}$ cycloalkyl $C_{1-3}$ alkyl;

$R^8$ is hydrogen or $C_{1-4}$ alkyl;

r is an integer from 2 to 5; and s is an integer from 3 to 5 with proviso that s is not 3 when r is 2.

The present compounds antagonize NK-1 receptors, that is; they bind to the receptors such that Substance P and other tachykinins are inhibited from binding to the NK-1 receptors. The compounds are useful as therapeutic agents in conditions characterized by excessive Substance P and other tachykinins expression, and thus, this disclosure provides methods of treating a subject afflicted with such a disorder. The present compounds are also useful as selective inhibitors of serotonin reuptake transporter protein.

DETAILED DESCRIPTION

The compounds of the present disclosure are useful in the treatment of central nervous system disorders and a myriad of other conditions by virtue of their activity as NK-1 receptor antagonists and/or their activity as selective serotonin reuptake inhibitors.

A compound is provided of formula (I) or isomer, a pharmaceutically acceptable salt or solvate thereof:

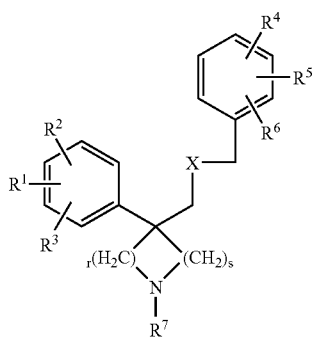

wherein $R^1$, $R^2$, $R^3$, $R^4$, $R^5$ and $R^6$ independently are hydrogen, $C_{1-4}$ alkyl, $C_{1-4}$ alkoxy, fluoro $C_{1-4}$ alkyl, halogen or cyano; X is independently selected from O, S and $NR^8$; $R^7$ is hydrogen, $C_{1-4}$ alkyl, $C_{3-6}$ cycloalkyl, or $C_{3-6}$ cycloalkyl $C_{1-3}$ alkyl; $R^8$ is hydrogen or $C_{1-4}$ alkyl; r is an integer from 2 to 5; and s is an integer from 3 to 5 with proviso that s is not 3 when r is 2.

"Alkyl" means saturated carbon chains, branched or unbranched having the specified number of carbons. The term "$(C_x\text{-}C_y)$ alkyl" where x and y are integers means an alkyl group having from x to y carbon atoms. The term "$C_{1-4}$ alkyl" means an alkyl group having from 1 to 4 carbon atoms and includes, without limitation groups such as methyl, ethyl, n-propyl, isopropyl, methylpropyl, n-butyl, t-butyl, isobutyl and sec-butyl. Derived expressions such as $C_{1-4}$ alkoxy are to be construed accordingly.

The term "$C_{3-6}$ cycloalkyl" as used herein means a carbon cyclic ring system having from 3 to 6 carbon atoms and includes cyclopropyl, cyclobutyl, cyclopentyl, cyclohexyl and the like. The term "fluoro $C_{1-4}$ alkyl" means a $C_{1-4}$ group in which one or more (in particular 1-3) hydrogen atoms have been replaced by fluorine atoms and includes without limitation trifluoromethyl, fluoromethyl, trifluoromethylethyl, trifluoromethylpropyl and the like.

"Halo" or "halogen" as used herein includes fluorine, chlorine, bromine, and iodine.

References hereinafter to a compound according to the present disclosure include both compounds of formula (1) and their pharmaceutically acceptable salts and solvates. The solvates may for example be hydrates.

Preferably $R^7$ is hydrogen.
Preferably r is 3 and s is 3; or r is 2 and s is 4.
Preferably X is oxygen and $R^7$ is hydrogen.
In a preferred embodiment, X is oxygen, $R^4$ and $R^5$ are each $CF_3$ and are each in the meta position with respect to —$CH_2X$— and $R^6$ is hydrogen and r is 3 and s is 3.

Specific compounds of the present disclosure are:
4-((3,5-bis(trifluoromethyl)benzyloxy)methyl)-4-phenylazocane and
5-((3,5-bis(trifluoromethyl)benzyloxy)methyl)-5-phenylazocane
or pharmaceutically acceptable salt and solvate thereof.

As the compounds of the present disclosure possess asymmetric carbon atoms, the present invention includes all "isomers" which means all possible stereoisomers, geometric isomers, diastereoisomers, enantiomers, anomers and optical isomers of the compounds of Formula I as described herein and in the claims. The use of a single designation such as (R) or (S) is intended to include mostly one stereoisomer at the position indicated. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The possible enantiomeric forms may also be separated by fractionation through chiral high pressure liquid chromatography columns.

The compounds may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. In the case of a sublingual formulation a saccharin salt or maleate salt may be of particular benefit. The compounds may be hydrated or non-hydrated.

As described in International Applications WO 2004/005255 and WO2004/005256, by virtue of their activity as tachykinin (especially NK-1 receptor) antagonists, the compounds of formula (I) are of value in the treatment of a wide variety of clinical conditions which are characterized by the presence of an excess tachykinin, in particular, substance P activity.

As previously stated, compounds of the present disclosure are useful in the treatment of central nervous system disorders, particularly in the treatment or prevention of depression and/or in the treatment of anxiety.

Depression includes, but, is not limited to Major Depressive Disorders (MDD), including bipolar depression, unipolar depression, single or recurrent major depressive episodes, recurrent brief depression, catatonic features, melancholic features including feeding disorders, such as anorexia, weight loss, atypical features, anxious depression, or postpartum onset.

Other central nervous system disorders encompassed within the term MDD include neurotic depression, post-traumatic stress disorders (PTSD) and social phobia; with early or late onset dementia of the Alzheimer's type, with depressed mood; vascular dementia with depressed mood; mood disorders and tolerance induced by drugs such as alcohol, amphetamines, cocaine, inhalants, opioids, sedatives, anxiolytics and other substances; schizoaffective disorder of the depressed type; and adjustment disorder with depressed mood.

Compounds of the disclosure are also useful in the treatment or prevention of schizophrenic disorders including paranoid schizophrenia, disorganized schizophrenia, catatonic schizophrenia, undifferentiated schizophrenia, residual schizophrenia.

The term anxiety includes, but is not limited to disorders, such as panic disorders, agoraphobia, phobias, obsessive-compulsive disorder, stress disorders including post-traumatic stress disorders, generalized anxiety disorders, acute stress disorders and mixed anxiety-depression disorders.

Compounds of the disclosure are also useful in the treatment or prevention of the cognitive disorders. Cognitive disorders include dementia, amnesia disorders and cognitive disorders not otherwise specified.

Furthermore, compounds of the disclosure are also useful as memory and/or cognition enhancers in healthy humans with no cognitive and/or memory deficit.

In addition, compounds of the disclosure are useful as analgesics. In particular, they are useful in the treatment of traumatic pain such as postoperative pain; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, peripheral neuropathy, diabetic neuropathy, chemotherapy-induced neuropathy, AIDS-related neuropathy, various forms of headache such as migraine, acute or chronic tension headache, cluster headaches, maxillary sinus pain, cancer pain; pain of bodily origin; gastrointestinal pain; sport's injury pain; dysmennorrhoea; menstrual pain; meningitis; musculoskeletal pain; low back pain e.g. spinal stenosis; prolapsed disc; sciatica; angina; ankylosing spondyolitis; gout; burns; scar pain; itch and thalamic pain such as post stroke thalamic pain.

Compounds of the disclosure are also useful in the treatment of sleep disorders including insomnia, sleep apnea, narcolepsy, and circadian rhymic disorders.

Compounds of the present disclosure are also useful as anti-inflammatory agents. In particular, they are useful in the treatment of inflammation in asthma, influenza and chronic bronchitis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the disclosure are also useful in the treatment of allergic disorders, in particular allergic disorders of the skin such as urticaria, and allergic disorders of the airways such as rhinitis.

Compounds of the disclosure are also useful in the treatment of emesis, i.e. nausea, retching and vomiting. Emesis includes acute emesis and anticipatory emesis. The compounds of the disclosure are useful in the treatment of emesis however induced. For example, emesis may be induced by drugs such as cancer chemotherapeutic agents such as alkylating agents, e.g. cyclophosphamide and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; increased intercranial pressure; decreased intercranial pressure (e.g. altitude sickness); opioid analgesics, such as morphine; and gastro-oesophageal reflux disease (GERD) such as erosive GERD and symptomatic GERD or non erosive GERD, acid indigestion, over-indulgence of food or drink, acid stomach, sour stomach, heartburn, such as episodic heartburn, nocturnal heartburn, and meal-induced heartburn, dyspepsia and functional dyspepsia.

The compounds of the disclosure are also useful in premenstrual dysphoric disorder (PMDD), in chronic fatigue syndrome and multiple sclerosis.

A compound is provided of formula (I) or a pharmaceutically acceptable salt or solvate thereof for use in therapy, in particular in human medicine.

In an alternative or further aspect there is provided a method for the treatment of a mammal, including man, in particular, in the treatment of conditions mediated by tachykinins, including substance P and other neurokinins and/or by selective inhibition of the serotonin reuptake transporter protein comprising administration of an effective amount of a compound of formula (I) or a pharmaceutically acceptable salt thereof.

In a further aspect of the disclosure is provided a method for the treatment of a mammal, including man, in particular in the treatment of depression and/or anxiety which method comprises administration of an effective amount of a compound of formula (I) or a pharmaceutically acceptable salt or solvate thereof.

The instantly recited compounds can be administered in such oral dosage forms as tablets, capsules (each of which includes sustained release or timed release formulations), pills, powders, granules, elixirs, tinctures, suspensions, syrups and emulsions. The compounds may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. The compounds can also be administered in intranasal form by topical use of suitable intranasal vehicles, or by transdermal routes, using transdermal skin patches. When the compounds are administered transdermally the dosage will be continuous throughout the dosage regimen.

The dosage and dosage regimen and scheduling of a compounds of the present disclosure must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Compounds of the present disclosure may be synthesized according to the general schemes provided below. Variables provided in the scheme below are defined in accordance with the description of compounds of the above Formulae unless otherwise specified.

Scheme 1 describes the synthesis of compounds of formula I wherein X is oxygen, r is (n+1) or (n+2), and s is m or (m+1), wherein m is an integer from 2 to 4, and n is an integer from 1 to 4, provided that n is not 1 when m is 2. Appropriately substituted phenylacetonitrile 3 underwent sequential alkylation with alkyl bromide or chloride using a base such as sodium hydride which provided 4. Compound 4 was converted to 5 by means of ring-closing metathesis (R. H. Grubbs and S. Chang, *Tetrahedron,* 1998, 54, 4413-4450, T. M. Trnka and R. H. Grubbs, *Acc. Chem. Res.* 2001, 34, 18-29). Reduction of 5 with diisobutylaluminum hydride gave aldehyde 6, which was further reduced to alcohol 7 using diisobutylaluminum hydride, lithium aluminum hydride or sodium borohydride. Compound 7 was treated with sodium hydride and appropriately substituted benzylbromide to furnish 8. This compound was converted to alcohol 9 via hydroborationoxidation (D. H. Hodgson et. al. *Tetrahedron*, 1999, 55, 10815-10834), and the hydroxyl group in 9 was oxidized to give ketone 10 using pyridinium chlorochromate. Schmidt rearrangement of 11 with hydrazoic acid in trifluoroacetic acid gave two lactams: 11 and 12 (A. G. Schultz et. al. *J. Med. Chem.* 1996, 39, 1956-1966). Lactams 11 and 12 were reduced with borane-THF complex to furnish amines 13 and 14, respectively. Compounds 13 and 14 were converted to Ia and Ib, respectively, via reductive alkylation with appropriate aldehydes.

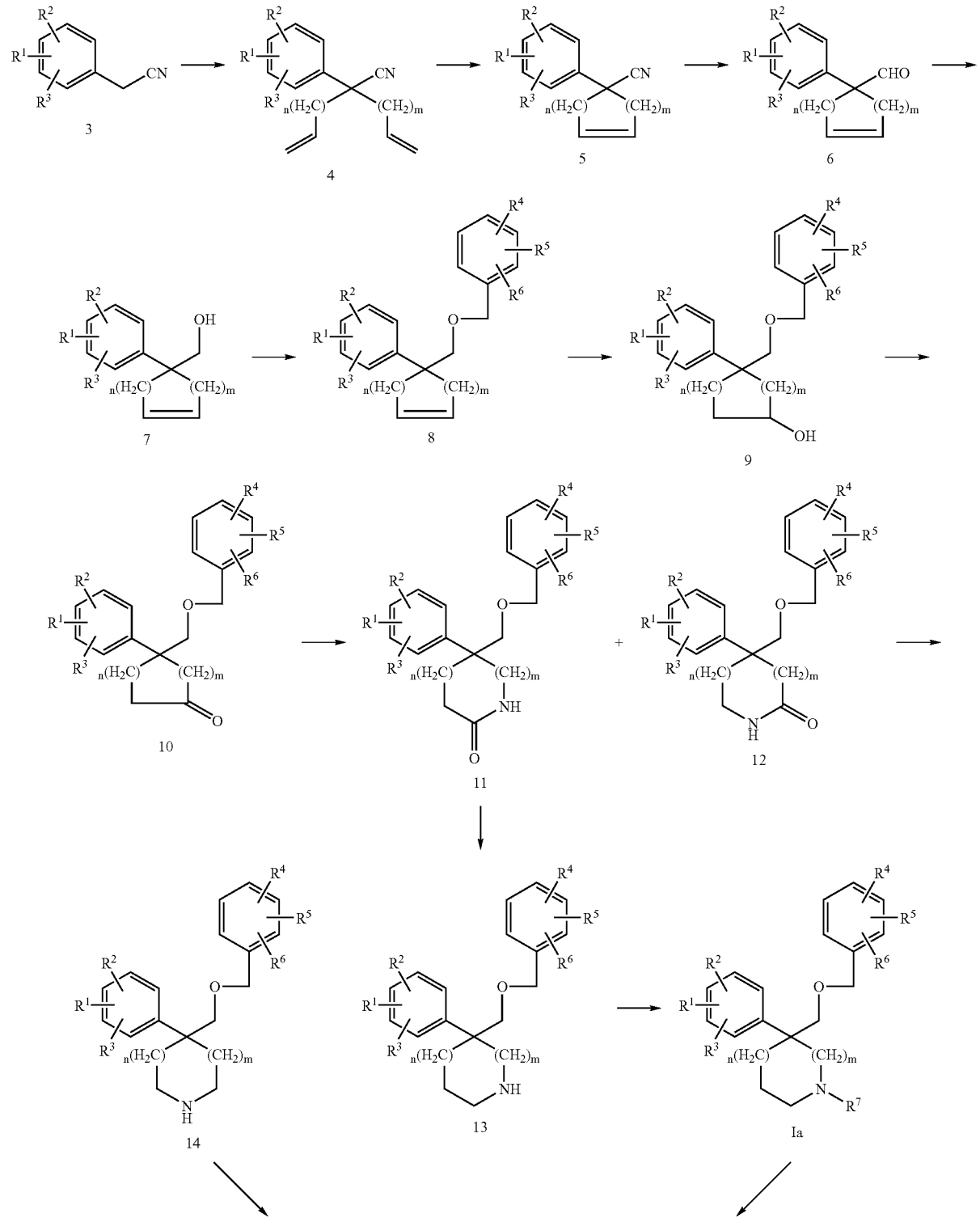

Scheme 1

-continued

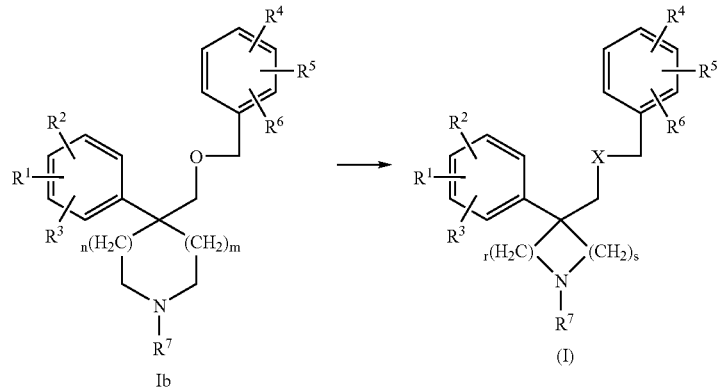

Scheme 2 describes the synthesis of compounds of formula I wherein X is NR8, r is (n+1) or (n+2), and s is m or (m+1), wherein m is an integer from 2 to 4, and n is an integer from 1 to 4, provided that n is not 1 when m is 2. Aldehyde 6 from Scheme 1 underwent reductive alkylation with appropriately substituted benzylamine to provide 17. The conversion of 17 to Ic and Id was carried out in a similar manner to that of 8 to Ia and Ib as shown in Scheme 1.

Scheme 3 describes the synthesis of compounds of formula I wherein X is sulfur, r is (n+1) or (n+2), and s is m or (m+1), wherein m is an integer from 2 to 4, and n is an integer from 1 to 4, provided that n is not 1 when m is 2. Alcohol 7 was converted to 20 wherein L is a mesyl group or tosyl group by treatment with mesyl chloride or tosyl chloride, respectively, in the presence of a base such as triethylamine. Exposure of

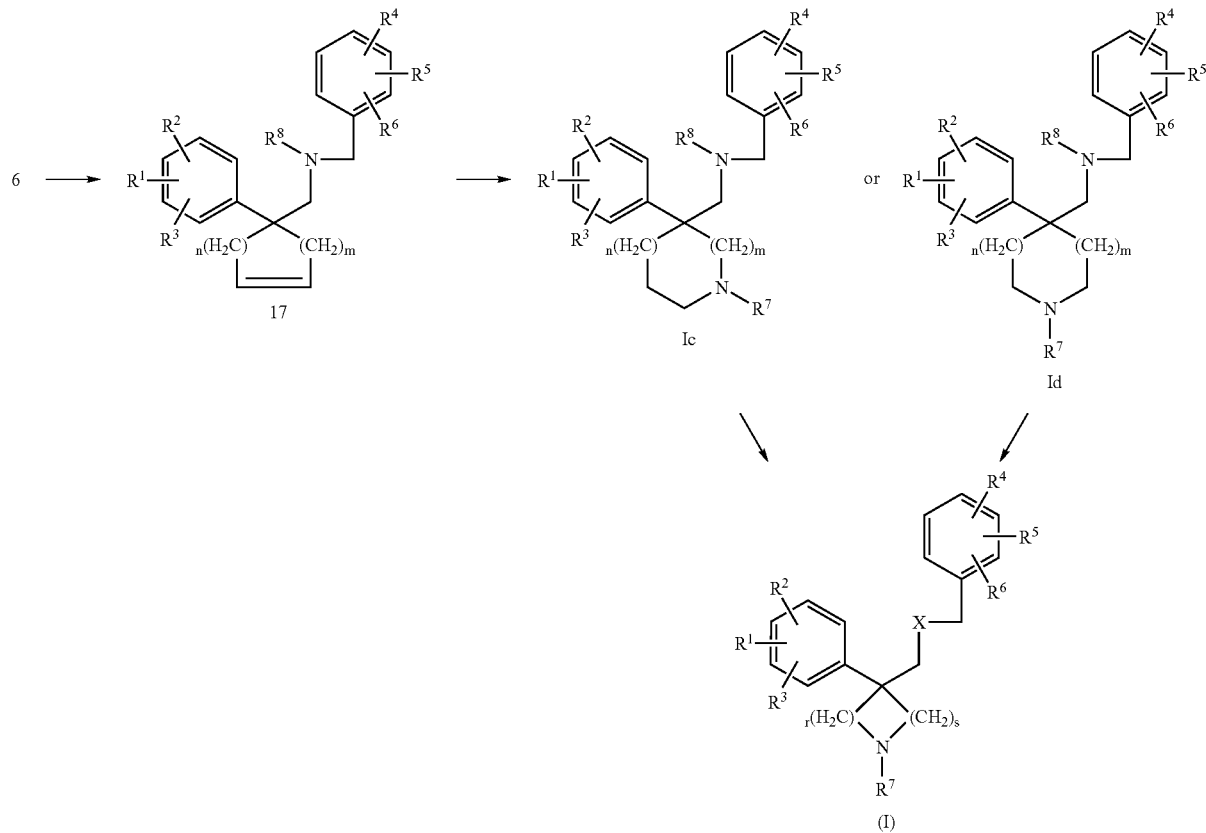

20 with appropriately substituted benzylthiol provided compounds of formula 21. The conversion of 21 to Ie and If was carried out in a similar fashion to that of 8 to Ia and Ib as shown in Scheme 1.
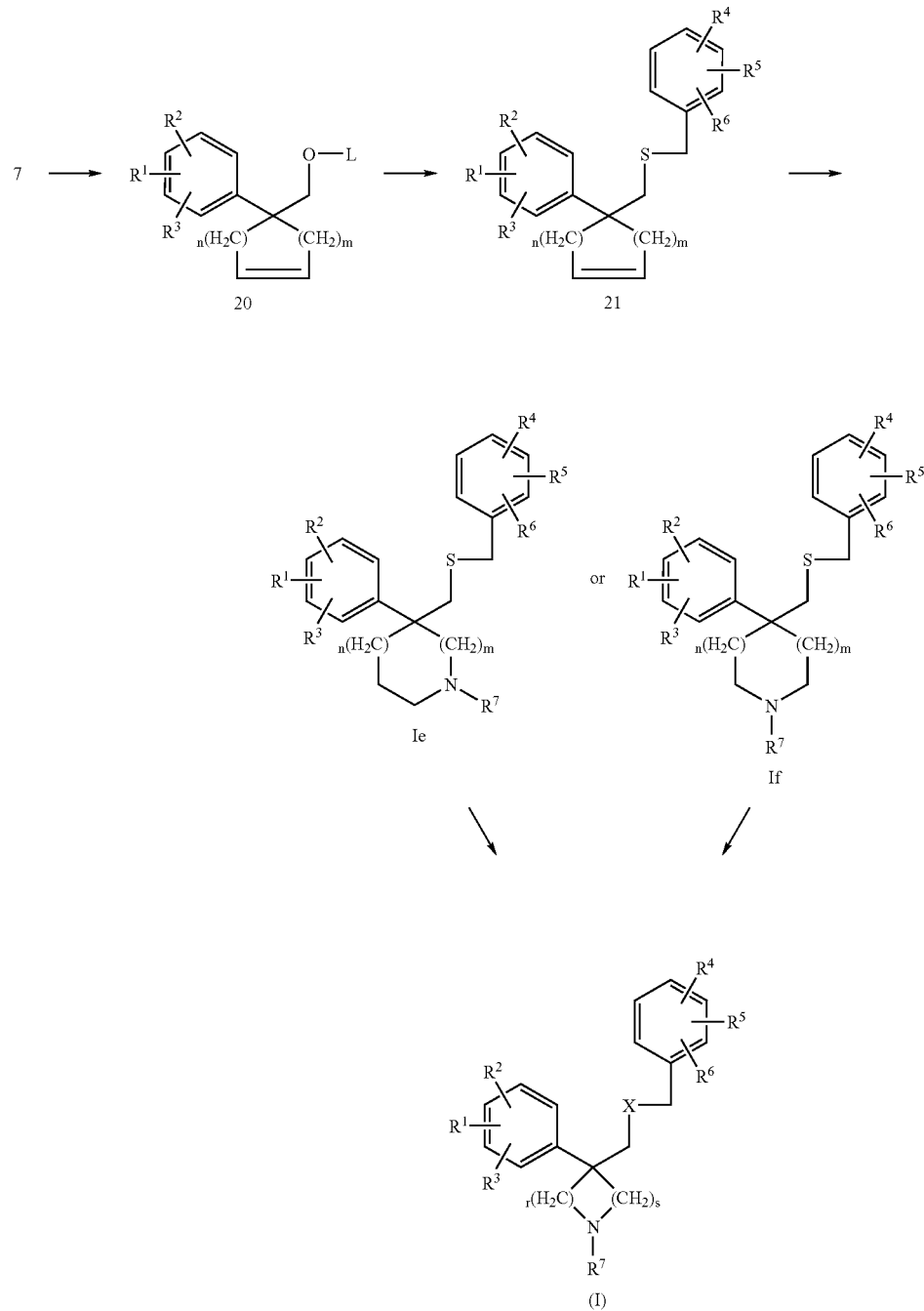

EXAMPLE 1

4-((3,5-bis(trifluoromethyl)benzyloxy)methyl)-4-phenylazocane

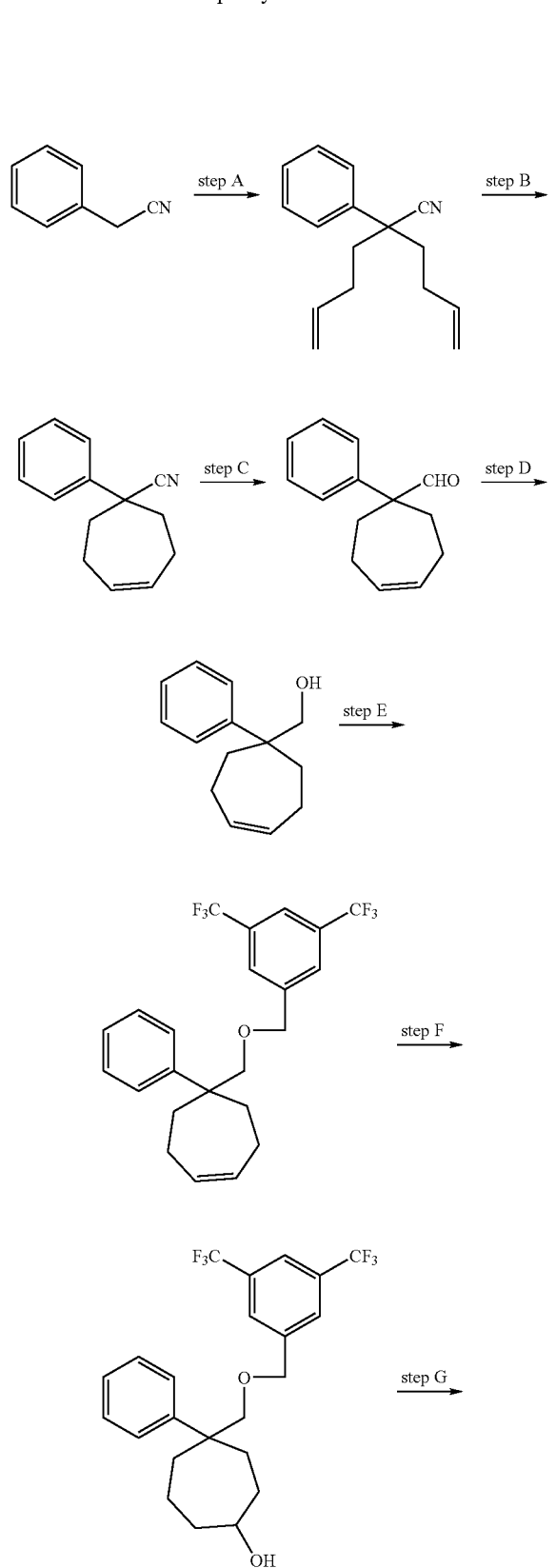

Step A: 2-Butyl-2-phenylhex-5-enenitrile

To a solution of 2-phenylacetonitrile (1 mL) in DMF (1.0 mL) at 0° C. was added sodium hydride (95% oil dispersion, 547 mg) and the resulting suspension was stirred at 0° C. for 10 min. 4-Bromobut-1-ene (2.2 mL) was added, and the reaction mixture was stirred at room temperature for 2 h. Saturated sodium chloride was added followed by ethyl acetate, the aqueous layer was extracted with ethyl acetate. The combined organic layers were dried over anhydrous sodium sulfate and filtered, and the filtrate was evaporated in vacuo. The residue was purified by silica gel flash chromatography eluting with 10% ethyl acetate/90% hexanes to give the title compound as an oil (773 mg). $^1$H NMR (400 MHz, CDCl$_3$) δ 1.8-2.3 (8H, m), 4.95 (4H, m), 5.73 (2H, m), and 7.31 (5H, m).

Step B: (Z)-1-phenylcyclohept-4-enecarbonitrile

To a solution of methyl 2-butyl-2-phenylhex-5-enenitrile (733 mg, step A) in dichloromethane (65 mL) was added benzylidene-bis(tricyclhexylphosphine) dichlororuthenium (134 mg) and the resulting suspension was heated under reflux for 1 h. The solvent was removed in vacuo to give the title compound. The crude product was used for the reduction to the aldehyde without purification. $^1$H NMR (400 MHz, CDCl$_3$) δ 1.93 (2H, t, J=12.4 Hz), 2.11 (2H, m), 2.30 (2H, m), 2.57 (2H, t, J=12.0 Hz), 5.91 (2H, m), 7.38 (5H, m).

Step C: (Z)-1-phenylcyclohept-4-enecarbaldehyde

To a solution of (Z)-1-phenylcyclohept-4-enecarbonitrile from step B in toluene (15 mL) at −78° C. was added diisobutylaluminum hydride (1.0 M solution in toluene, 4.88 mL), and the resulting solution was stirred at −78° C. for 2 h. Saturated ammonium chloride was added drop wise followed by ethyl acetate. The aqueous layer was extracted with ethyl acetate, and the combined organic layers were washed with brine, dried over anhydrous sodium sulfate and filtered. The filtrate was evaporated in vacuo to give the title compound. $^1$H NMR (400 MHz, CDCl$_3$) δ 2.21 (6H, m), 2.37 (2H, m), 5.69 (2H, s), 7.30 (5H, m), and 9.38 (1H, s).

Step D: (Z)-(1-phenylcyclohept-4-enyl)methanol

To a solution of (Z)-1-phenylcyclohept-4-enecarbaldehyde (22 mg, step C) in methanol (1 mL) was added sodium borohydride (8 mg), and the resulting mixture was stirred at room temperature for 1 h. Methanol was removed in vacuo, water and ethyl acetate were added. The aqueous layer was extracted with ethyl acetate, and the combined organic layers were washed with brine, dried over anhydrous sodium sulfate and filtered. The filtrate was evaporated in vacuo to give the title compound as an oil. $^1$H NMR (400 MHz, CDCl$_3$) δ 1.91 (2H, m), 2.20 (6H, m), 3.55 (2H, s), 5.68 (2H, m), 7.35 (5H, m). $^{13}$C NMR (CDCl$_3$, 100 MHz) δ 24.0, 32.9, 47.3, 71.7, 126.3, 127.4, 128.6, 131.2, 144.3.

Step E: (Z)-5-((3,5-bis(trifluoromethyl)benzyloxy)methyl)-5-phenylcyclohept-1-ene To a solution of (Z)-(1-phenylcyclohept-4-enyl)methanol (9 mg) from step D and 3,5-(bis-trifluoromethyl)benzyl bromide (17 µL) in DMF (0.2 mL) at 0° C. was added sodium hydride (95% oil dispersion, 2 mg) and the resulting suspension was stirred at room temperature for 30 min. Water was added followed by ethyl acetate, and the aqueous layer was extracted with ethyl acetate. The combined organic layers were dried over anhydrous sodium sulfate and filtered, and the filtrate was evaporated in vacuo. The residue was purified by preparative TLC eluting with 10% ethyl acetate/90% hexanes to give the title compound as an oily material (10 mg). $^1$H NMR (400 MHz, CDCl$_3$) δ 1.98 (2H, m), 2.15 (4H, m), 2.28 (2H, m), 3.47 (2H, s), 4.42 (2H, s), 5.67 (2H, m), 7.22 (1H, m), 7.34 (2H, m), 7.39 (2H, m), 7.54 (2H, s), and 7.72 (1H, s). HRMS m/z calcd. for C$_{23}$H$_{21}$F$_6$O (M−H)$^−$ 427.1497, found 427.1481.

Step F: 4-((3,5-bis(trifluoromethyl)benzyloxy)methyl)-4-phenylcycloheptanol

To a solution of (Z)-5-((3,5-bis(trifluoromethyl)benzyloxy)methyl)-5-phenylcyclohept-1-ene (56 mg) from step E in THF (0.55 mL) at 0° C. was added borane-tetrahydrofuran complex (1.5 M solution, 0.17 mL) drop wise, and the resulting solution was warmed to room temperature and stirred at room temperature for 12 h. The reaction mixture was cooled to 0° C., and water (10.50 mL) was added slowly followed by 30% hydrogen peroxide (0.19 mL) and 1 N sodium hydroxide (0.30 mL). The resulting solution was stirred at room temperature for 5 min, and ethyl acetate (2.0 mL) was added. The aqueous layer was extracted with ethyl acetate. The combined organic layers were dried over anhydrous sodium sulfate and filtered, and the filtrate was evaporated in vacuo. The residue was purified by preparative TLC eluting with 40% ethyl acetate/60% hexanes to give the title compound as an oily material (27 mg). $^1$H NMR (400 MHz, CDCl$_3$) δ 1.3-2.4 (m), 3.40 (s), 3.44 (s), 4.43 (s), 7.32 (m), 7.56 (s), and 7.73 (s). HRMS m/z calcd for C$_{23}$H$_{23}$F$_6$O2 (M−H)$^−$ 445.1602, found 445.1607.

Step G: 4-((3,5-bis(trifluoromethyl)benzyloxy)methyl)-4-phenylcycloheptanone

To a solution of 4-((3,5-bis(trifluoromethyl)benzyloxy)methyl)-4-phenylcycloheptanol (26 mg, step F) in dichloromethane (0.5 mL) at room temperature were added pyridinium chlorochromate (25 mg) and powdered 4A° molecular sieves (26 mg), and the resulting mixture was stirred at room temperature for 1.5 h and then filtered through a small pad of silica gel. The filtrate was evaporated in vacuo and the residue was purified by preparative TLC eluting with 30% ethyl acetate/70% hexanes to give the title compound as an oily material (21 mg). $^1$H NMR (400 MHz, CDCl$_3$) δ 1.74 (3H, m), 1.98 (1H, dd, J=11.6, 1.2 Hz), 2.48 (6H, m), 3.37 (1H, d, J=8.8 Hz), 3.39 (1H, d, J=8.8 Hz), 4.42 (2H, s), 7.28 (1H, m), 7.35 (4H, m), 7.56 (2H, m), and 7.74 (1H, s). HRMS m/z calcd. for C$_{23}$H$_{21}$F$_6$O2 (M−H)$^−$ 443.1446, found 443.1457.

Step H: 6-((3,5-bis(trifluoromethyl)benzyloxy)methyl)-6-phenylazocan-2-one

To a solution of 4-((3,5-bis(trifluoromethyl)benzyloxy)methyl)-4-phenylcycloheptanone (13 mg, step G) in TFA (50 µL) was added sodium azide (3.0 M solution in water, 21 µL) and the resulting solution was heated at 65° C. in a sealed vial for 1 h. TFA was removed in vacuo, saturated sodium bicarbonate solution was added followed by ethyl acetate. The aqueous layer was extracted with ethyl acetate. The combined organic layers were dried over anhydrous sodium sulfate and filtered, and the filtrate was evaporated in vacuo. The residue was purified by preparative TLC eluting with 60% ethyl acetate/40% hexanes to give two isomers: 6-((3,5-bis(trifluoromethyl)benzyloxy)methyl)-6-phenylazocan-2-one (2.5 mg) and 5-((3,5-bis(trifluoromethyl)benzyloxy)methyl)-5-phenylazocan-2-one (2.5 mg).

6-((3,5-bis(trifluoromethyl)benzyloxy)methyl)-6-phenylazocan-2-one: $^1$H NMR (400 MHz, CDCl$_3$) δ 1.5-2.2 (7H, m), 2.63 (1H, dd, J=5.5, 115.0 Hz), 3.31 (1H, d, J=8.5 Hz), 3.37 (1H, d, J=8.5 Hz), 3.44 (1H, m), 3.77 (1H, m), 4.43 (1H, d, J=8.0 Hz), 4.46 (1H, d, J=8.0 Hz), 5.97 (1H, s), 7.26 (3H, m), 7.36 (2H, m), 7.49 (2H, s), and 7.73 (1H, s). $^{13}$C NMR (CDCl$_3$, 125 MHz) δ 22.9, 30.2, 31.8, 38.8, 40.4, 45.5, 71.8, 84.1, 121.5, 123.4 (q, J=262.5 Hz), 126.7, 127.1, 127.5, 128.5, 131.6 (q, J=37.5 Hz), 141.1 (d, J=25.0 Hz), 176.8.

5-((3,5-bis(trifluoromethyl)benzyloxy)methyl)-5-phenylazocan-2-one: $^1$H NMR (500 MHz, CDCl$_3$) δ 1.67 (1H, m), 1.85 (2H, m), 2.06 (2H, m), 2.49 (1H, m), 2.77 (4H, m), 3.33 (1H, d, J=8.5 Hz), 3.37 (1H, d, J=8.5 Hz), 4.34 (1H, d, J=4.34 (1H, d, J=13.0 Hz), 4.44 (1H, d, J=13.0 Hz), 5.61 (1H, s), 7.28 (3H, m), 7.38 (t, J=8.0 Hz), 7.50 (2H, s), and 7.73 (1H, s). $^{13}$C NMR (CDCl$_3$, 125 MHz) δ 27.6, 29.9, 30.1, 40.9, 45.4, 71.8, 83.7, 121.4, 123.4 (q, J=262.5 Hz), 126.6, 127.1, 127.5, 127.6, 128.4, 131.7 (q, J=37.5 Hz), 141.1 (d, J=25.0 Hz), 178.0.

Step I: 4-((3,5-bis(trifluoromethyl)benzyloxy)methyl)-4-phenylazocane

To a solution of 6-((3,5-bis(trifluoromethyl)benzyloxy)methyl)-6-phenylazocan-2-one (18 mg, step H) in THF (0.10 mL) at room temperature was added borane-THF complex (1.50 M solution in THF, 0.10 mL) and the resulting solution was heated at 65° C. in a sealed vial for 3 h. The solution was cooled to room temperature, and methanol (0.10 mL) was added slowly followed by 1N hydrochloric acid (0.10 mL), and the reaction mixture was heated at 65° C. for 2 h. The solvents were removed in vacuo, dichloromethane and 1N sodium hydroxide were added, and the aqueous layer was extracted with dichloromethane. The combined organic layers were washed with brine, dried over anhydrous sodium sulfate, and filtered. The filtrate was evaporated in vacuo to give the title compound as an oil. $^1$H NMR (400 MHz, CDCl$_3$) δ 1.58 (5H, m), 2.09 (3H, m), 2.30 (1H, m), 2.94 (4H, m), 3.44 (1H, d, J=8.8 Hz), 3.47 (1H, d, J=8.8 Hz), 4.42 (2H, s), 7.21 (1H, m), 7.37 (4H, m), 7.55 (2H, s), and 7.73 (1H, s). HPLC retention time (1.88 min, column: 4.6×50 mm XTERRA C18 S5, flow rate: 5 mL/min, gradient: 0-100% MeOH/H$_2$O 0.1% TFA over 2 min). MS: 446 (MH$^+$).

EXAMPLE 2

5-((3,5-bis(trifluoromethyl)benzyloxy)methyl)-5-phenylazocane

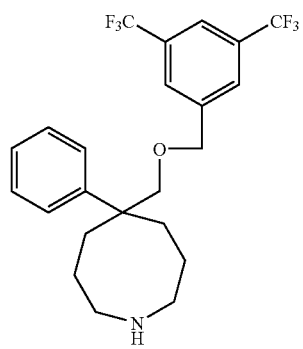

To a solution of 5-((3,5-bis(trifluoromethyl)benzyloxy)methyl)-5-phenylazocan-2-one (16 mg) in THF (0.10 mL) at room temperature was added borane-THF complex (1.50 M solution in THF, 93 µL) and the resulting solution was heated at 65° C. in a sealed vial for 3 h. The solution was cooled to room temperature, and methanol (0.10 mL) was added slowly followed by 1N hydrochloric acid (0.10 mL), and the reaction mixture was heated at 65° C. for 2 h. The solvents were removed in vacuo, dichloromethane and 1N sodium hydroxide were added, and the aqueous layer was extracted with dichloromethane. The combined organic layers were washed with brine, dried over anhydrous sodium sulfate, and filtered. The filtrate was evaporated in vacuo to give the title compound as an oil. $^1$H NMR (400 MHz, CDCl$_3$) δ 1.57 (4H, m), 1.87 (1H, broad, s), 2.09 (4H, m), 2.72 (2H, m), 2.88 (2H, m), 3.43 (2H, s), 4.41 (2H, s), 7.21 (1H, m), 7.39 (4H, m), 7.54 (2H, s), and 7.21 (1H, s). HPLC retention time (1.87 min, column: 4.6×50 mm XTERRA C18 S5, flow rate: 5 mL/min, gradient: 0-100% MeOH/H$_2$O 0.1% TFA over 2 min). MS: 446 (MH$^+$).

NK-1 Binding Method

U373 cells, a human glioblastoma-astrocytoma cell line that endogenously expresses the neurokinin-1 (NK-1) receptor, were grown in a monolayer culture at 37° C. in 5% CO$_2$ and fed with Minimum Essential Medium (MEM) supplemented with 10% fetal bovine serum. Membranes were prepared as follows: Cells were washed twice with ice-cold phosphate-buffered saline (pH 7.4) and then incubated for 5 to 10 minutes with ice-cold 10 mM Tris buffer (pH 7.4) containing 5 mM EDTA. Cells were removed from plates, homogenized, and centrifuged at 32,000×g for 20 minutes. The resulting supernatant was discarded, and the pellet resuspended by homogenization in 50 mM Tris buffer (pH 7.4) containing 1 mM EDTA and centrifuged at 32,000×g for 20 minutes. The resulting supernatant was discarded, and the pellet resuspended by homogenization in NK-1 binding assay buffer (50 mM Tris-HCL (pH 7.4), 3 mM MnCl$_2$, 200 µg/ml BSA, 5 µg/ml chymostatin, 40 µg/ml bacitracin and 4 µg/ml leupeptin).

On the day of an experiment the membrane preparation was thawed, homogenized and diluted with NK-1 binding assay buffer to the appropriate concentration. Competition binding assays were performed in 96 well plate format by incubating membranes (5-10 ug/well) with Bolton Hunter labeled [$^{125}$I] Substance P, at a concentration of 200 nM, and concentrations of drugs ranging from 10000 to 0.01 nM. Samples were incubated for 30 min at 20° C. then filtered through GF/B glass fiber filters (pretreated with 1% polyethyleneimine and 0.3% Triton X-100) using a Brandel cell harvester. The filters were then washed with 10 ml ice cold 50 mM Tris-HCL (pH 7.4) containing 3 mM MgCl$_2$. Non-specific was defined in the presence of 2 µM L-733,060 (a nonpeptide NK-1 antagonist). The amount of radioligand bound in the presence and absence of competitor was analyzed by plotting (−)log drug concentration versus the amount of radioligand specifically bound. The midpoint of the displacement curve (IC$_{50}$, nM), signifies the potency. K$_i$ values were calculated using the method of Cheng and Prusoff [Cheng, Y.-C. and Prusoff, W. H., *Biochemical Pharmacology*, Vol. 22, pp. 3099-3108, Pergamon Press (1973)].

Serotonin Transporter Binding Assay

HEK-293 cells that stably express human serotonin transporters (HEK-hSERT cells) were grown at 37° C. in 5% CO$_2$ as a monolayer in medium consisting of EMEM supplemented with 10% fetal bovine serum and G418 sulfate (500 µg/ml). To prepare membranes for radioligand binding experiments, cells were rinsed twice with phosphate-buffered saline (138 mM NaCl, 4.1 mM KCl, 5.1 mM Na$_2$PO$_4$, 1.5 mM KH$_2$O$_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 µl/plate) were incubated with 1 nM [$^3$H]-citalopram (specific activity=85 Ci/mmol) and increasing concentrations of test compounds for 1 hr at 25° C. in a total volume of 250 µl. The assay buffer consisted of 50 mM Tris (pH 7.4 at 25° C.), 120 mM NaCl and 5 mM KCl (pH 7.4 with conc. HCl). Plates were incubated for 1 hr at 25° C., then filtered through 0.5% PEI treated Whatman GF/B filters using a Brandel cell harvester. Filters were washed three times with 3 ml of ice-cold tris wash buffer. Non-specific binding was defined with 10 µM fluoxetine. Amount of radioligand bound in the presence and absence of competitor was analyzed by plotting (−)log drug concentration versus the amount of radioligand specifically bound. The midpoint of the displacement curve (IC$_{50}$, nM), signifies the potency. K$_i$ values were calculated using the method of Cheng and Prusoff Cheng and Prusoff [Cheng, Y.-C. and Prusoff, W. H., *Biochemical Pharmacology*, Vol. 22, pp. 3099-3108, Pergamon Press (1973)].

NK-1 binding results are shown in Table I below.

TABLE 1

| Example | NK-1 IC$_{50}$ | SERT IC$_{50}$ |
|---------|----------------|----------------|
| 1       | ***            | **             |
| 2       | ***            | **             |

*** IC$_{50}$ < 20 nM;
** 20 nM < IC$_{50}$ < 100 nM;
* 100 nM < IC$_{50}$ < 300 nM

In Table I, the compounds of Example 1,4-((3,5-bis(trifluoromethyl)benzyloxy)methyl)-4-phenylazocane, and Example 2,5-((3,5-bis(trifluoromethyl)benzyloxy)methyl)-5-phenylazocane, have activity for both NK-1 and SERT.

The above non-limiting examples serve to illustrate the preparation and use of compounds of the present disclosure.

What is claimed is:

1. A compound of Formula (I)

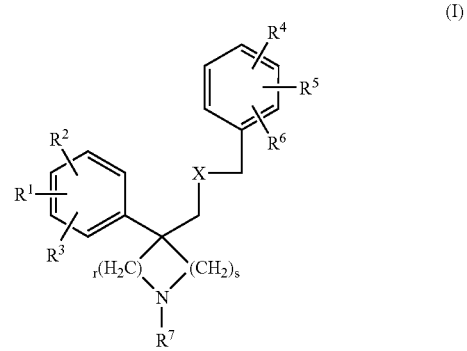

or an isomer, a pharmaceutically acceptable salt thereof wherein

R$^1$, R$^2$, R$^3$, R$^4$, R$^5$ and R$^6$ independently are hydrogen, C$_{1-4}$alkyl, C$_{1-4}$alkoxy, fluoroC$_{1-4}$alkyl, halogen or cyano;

X is O;

R$^7$ is hydrogen, C$_{1-4}$alkyl, C$_{3-6}$cycloalkyl or C$_{3-6}$cycloalkylC$_{1-3}$alkyl;

R$^8$ is hydrogen or C$_{1-4}$alkyl;

r is 2 and s is 4 or r is 3 and s is 3.

2. The compound of claim 1, wherein R$^7$ is hydrogen.

3. The compound of claim 1 wherein R$^4$ and R$^5$ are each independently CF$_3$ and R$^6$ is hydrogen.

4. The compound of claim 2 wherein R$^4$ and R$^5$ are each independently CF$_3$ and R$^6$ is hydrogen.

5. The compound of claim 1 wherein r is 2 and s is 4.

6. The compound of claim 1 wherein r is 3 and s is 3.

7. The pharmaceutical composition comprising a compound of claim 1, together with at least one pharmaceutically acceptable excipient.

* * * * *